(12) United States Patent
Chen et al.

(10) Patent No.: US 11,176,848 B1
(45) Date of Patent: Nov. 16, 2021

(54) TISSUE-MIMICKING MATERIAL FOR A MULTI-MODALITY IMAGING PHANTOM

(71) Applicant: ENDRA Life Sciences Inc., Ann Arbor, MI (US)

(72) Inventors: Charlton Chen, Northville, MI (US); Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 17/326,575

(22) Filed: May 21, 2021

Related U.S. Application Data

(60) Provisional application No. 63/032,044, filed on May 29, 2020.

(51) Int. Cl.
*G09B 23/28* (2006.01)
*G01R 33/58* (2006.01)
*A61B 5/00* (2006.01)
*A61B 8/00* (2006.01)

(52) U.S. Cl.
CPC .......... *G09B 23/286* (2013.01); *A61B 5/0035* (2013.01); *A61B 5/0093* (2013.01); *A61B 8/587* (2013.01); *G01R 33/58* (2013.01)

(58) Field of Classification Search
CPC .... G09B 23/286; G01R 33/58; A61B 5/0093; A61B 5/0035; A61B 8/587
See application file for complete search history.

(56) References Cited

U.S. PATENT DOCUMENTS

| | | | |
|---|---|---|---|
| 5,196,343 A | 3/1993 | Zerhouni et al. | |
| 5,625,137 A | 4/1997 | Madsen et al. | |
| 6,318,146 B1 * | 11/2001 | Madsen ............... | A61B 8/08 |
| | | | 324/308 |
| 6,352,860 B1 | 3/2002 | Madsen et al. | |
| 2002/0012999 A1 | 1/2002 | Madsen et al. | |
| 2003/0086535 A1 | 5/2003 | Teppaz et al. | |
| 2005/0227364 A1 | 10/2005 | Madsen et al. | |
| 2017/0293011 A1 | 10/2017 | Mirowski et al. | |
| 2020/0061552 A1 | 2/2020 | Ohmae et al. | |

OTHER PUBLICATIONS

D'Souza et al. "Tissue mimicking materials for a multi-imaging modality prostate phantom". Apr. 2001, Medical Physics, vol. 28, Issue 4, pp. 688-700. (Year: 2001).*

Kari Rodriguez; PCT International Search Report and Written Opinion; dated Aug. 24, 2021; 8 pages total; WIPO Alexandria, VA, United States.

(Continued)

*Primary Examiner* — Peter Luong
(74) *Attorney, Agent, or Firm* — Stanley E. Jelic

(57) ABSTRACT

A multi-modality fatty tissue mimicking material for phantoms for use with thermoacoustic imaging, ultrasound imaging and magnetic resonance imaging, which includes: an aqueous mixture of a 3% to 18% thickening agent, a 1% to 30% protein powder, a 0.1% to 2% ionic salt, a 30% to 85% water, and a 0% to 60% oil by weight, wherein the oil percentage corresponds to the fat percentage in tissue, further wherein the ionic salt percentage corresponds to an imaginary part of complex permittivity in tissue, and further wherein the water, oil and protein powder percentages correspond to the real part of complex permittivity in tissue.

6 Claims, 3 Drawing Sheets

(56) References Cited

OTHER PUBLICATIONS

Wikipedia Article "Gelatin"; May 1, 2020 (May 1, 2020); retrieved from "https://en.wikipedia.org/w/index.php?title=Gelatin&oldid=954339867"; p. 1 para 1; p. 2 table; p. 4 para 4.
Webb; "Dielectric Materials in Magnetic Resonance"; Concepts in Magnetic Resonance; Part A; vol. 38A, No. 4; pp. 148-184; Jun. 20, 2011 (Jun. 20, 2011).

* cited by examiner

TISSUE-MIMICKING MATERIAL FOR A MULTI-MODALITY IMAGING PHANTOM

CROSS-REFERENCE TO RELATED APPLICATIONS

This application claims the priority benefit of U.S. Provisional Patent Application No. 63/032,044, filed on May 29, 2020, the entirety of which is incorporated herein by reference.

FIELD

This application relates to a phantom that can be imaged utilizing different imaging methods. In particular, the phantom can be imaged utilizing ultrasound, magnetic resonance imaging (MRI), and thermoacoustics.

BACKGROUND

A tissue-mimicking material is typically designed to be effective with a particular imaging modality. For example, a tissue-mimicking material designed for an ultrasound phantom would have the same ranges of speed of sound, attenuation coefficients, and backscatter coefficients as soft tissue.

Special cases arise when one imaging modality is being used to certify another imaging modality. For example, magnetic resonance imaging (MRI) can be used to certify the accuracy of a thermoacoustic imaging system.

A thermoacoustic imaging system typically works in conjunction with an ultrasound system. The ultrasound system maps (provides location coordinates) of a region of tissue. The thermoacoustic system then determines tissue parameters at specific locations of a region of tissue.

Therefore, it would be beneficial and there exists a need to have a tissue-mimicking material that is useful for calibrating, verifying or certifying for multiple modalities: thermoacoustic imaging, ultrasound imaging, and MRI.

SUMMARY

In one embodiment, a multi-modality fatty tissue mimicking material (or multi-modality quantitative fatty tissue mimicking material) for phantoms for use with thermoacoustic imaging, ultrasound and MRI comprising: an aqueous mixture of a 3% to 18% thickening agent, a 1% to 30% protein powder, a 0.1% to 2% ionic salt, a 30% to 85% water, and a 0% to 60% oil by weight, wherein the oil percentage corresponds to the fat percentage in tissue, further wherein the ionic salt percentage corresponds to an imaginary part of complex permittivity in tissue, and further wherein the water, oil and protein powder percentages correspond to the real part of complex permittivity in tissue.

Different embodiments of thickening agent can be but are not limited to: Agar, Agarose, Gelatin, Polyvinyl Alcohol, Sodium Polyacrylate, Sodium Alginate, Acrylamide (for example Zerdine® from CIRS, Inc.: U.S. Pat. No. 5,196,343), Polyacrylamide, Hydroxyethyl Cellulose, Gellan Gum, Guar Gum (for example TX-150 and TX-151 from Oil Center Research), Xanthan Gum, Gum Arabic, Gum Tragacanth, Pectin, Carrageenan, Arrowroot, Starches, some combination thereof, or the like.

Different embodiments of protein powder can be but are not limited to: wherein the protein powder is selected from a group consisting of Tyrosine, Proline, Casein, Glycine, Arginine, Methionine, Cystine, Cysteine, Glutamine, Valine, Carnosine, Theanine, Citrulline, Serine, Histidine, Carnitine, Norvaline, Malate, Leucine, Threonine, Ornithine, Albumin, Collagen, Whey, Soy, Pea, Rice, Hemp, and some combination thereof.

Different embodiments of ionic salt can be but are not limited to: Sodium Chloride, Sodium Phosphate, Sodium Fluoride, Sodium Bicarbonate (baking soda), Sodium Carbonate, Sodium Sulfite, Sodium Hydroxide (Lye/Caustic Soda), Trisodium Citrate, Potassium Iodide, Potassium Phosphate (Mono- Di- Tri-), Potassium Chloride, Magnesium Sulfate (Epsom Salt), Magnesium Hydroxide, Calcium Carbonate, Aluminum Hydroxide, Silver Iodide, some combination thereof, or the like.

Different embodiments of water can be but are not limited to: Deionized, Distilled, Filtered, Tap, some combination thereof, or the like.

In a separate embodiment, high permittivity alternatives to water are substituted for water. Embodiments include but are not limited to: Propylene Glycol, Propylene Carbonate, Ethylene Glycol, some combination thereof, or the like.

Different embodiments of oil can be but are not limited to: Vegetable Oil, Animal Fat, or a synthetic alternative.

Different embodiments of vegetable oil can be but are not limited to: Peanut Oil, Olive Oil, Soybean Oil, Sesame Oil, Canola Oil, Safflower Oil, Sunflower Oil, Linseed Oil, Rapeseed Oil, Cottonseed Oil, Jojoba Oil, Coconut Oil, *Theobroma* Oil, Avocado Oil, Castor Oil, Corn Oil, Palm Oil, some combination thereof, or the like.

Different embodiments of animal fat can be but are not limited to: Tallow, Lard, Fish Oil, Suet, Ghee, Cheese, Butter, Milk, some combination thereof, or the like.

Different embodiments of a synthetic alternative can be but are not limited to: Mineral Oil, Paraffin Oil, some combination thereof, or the like.

In separate embodiments, a 0-5% by weight preservative, antifungal, or antibacterial agent is added to the mimicking material.

BRIEF DESCRIPTION OF THE DRAWINGS

Embodiments will now be described more fully with reference to the accompanying drawings in which.

DETAILED DESCRIPTION OF THE EMBODIMENTS

Figure 1:
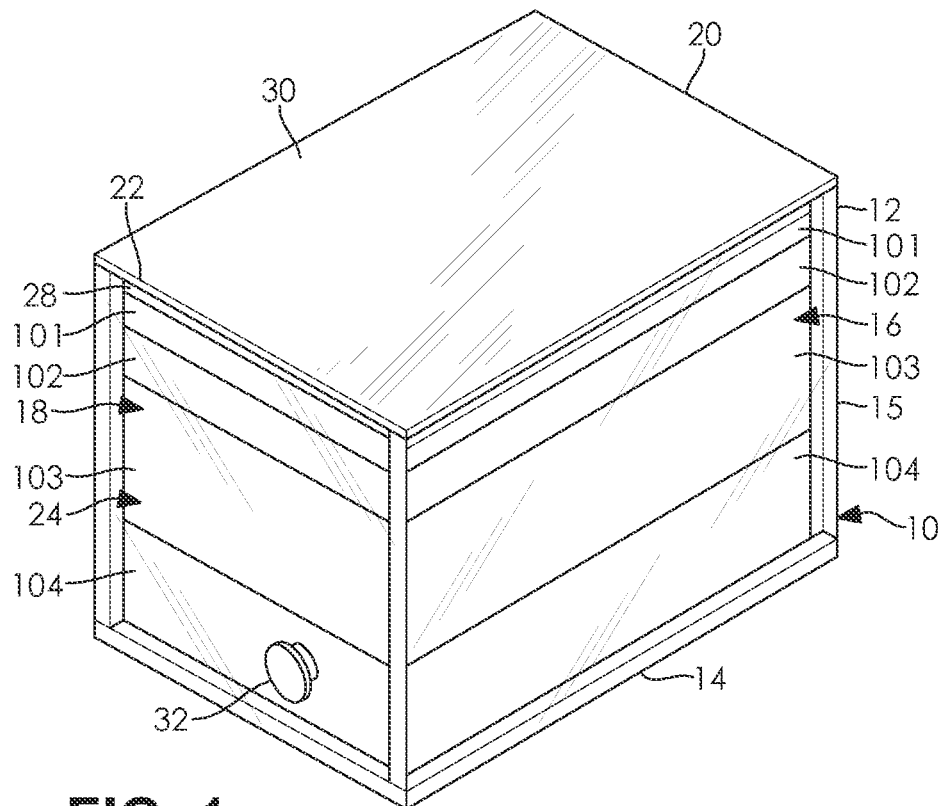
FIG. 1 shows a perspective view of a multi-modality imaging phantom embodiment.

The present disclosure discusses a fatty tissue-mimicking material for multi-modality imaging phantoms. These phantoms can also be used for fat quantification. An imaging phantom is used to evaluate, analyze and tune the performance of medical imaging equipment. It contains materials that mimic the properties of tissue in the human body and is more readily available and consistent then the use of a living subject or cadaver. For example, an imaging phantom can resemble bodily tissue in mass, composition and/or dimensions. An imaging phantom can resemble bodily tissue in its interaction with acoustic, thermal, and/or electromagnetic radiation. Potential imaging modes include thermoacoustic imaging, ultrasound, and MRI.

One objective of the material discussed in this disclosure is to quantitatively mimic fat in human liver tissue (hepatic steatosis, non-alcoholic fatty liver disease) in multiple modalities simultaneously. Specifically, in thermoacoustic imaging, ultrasound imaging, and magnetic resonance imaging (MRI). Fat content can be quantitatively analyzed using magnetic resonance (MR) spectroscopy, MRI Proton Density Fat Fraction (MRI-PDFF) and thermoacoustic fat quantification.

In one embodiment, the purpose of tissue-mimicking phantoms is to replicate the properties of human tissue that will be detected by medical imaging devices. These phantoms can be used for training, system testing, validation, verification, quality assurance, and the like.

Generally, phantoms are made for one modality. For example, an ultrasound tissue-mimicking phantom will have the acoustic properties of the body tissue that it is trying to simulate.

Multi-modality phantoms are useful for multi-modality imaging techniques. In thermoacoustic imaging, both the dielectric properties and acoustic properties of tissue are relevant.

Thermoacoustic imaging can be used to quantify the fat content present in the fatty tissue, for example in liver tissue. Alternatively, the fat content of the liver can be quantified using Magnetic Resonance (MR) fat quantification techniques, for example MRI-PDFF. A thermoacoustic phantom that is compatible with MR fat quantification techniques can be used for verification and validation.

Different imaging modalities are functions of different parameters or properties. For magnetic resonance imaging, complex permittivities (both real part and imaginary part) at RF and microwave frequencies impact deposition of electromagnetic power in a measurable way. For ultrasound imaging, speed of sound, acoustic attenuation, and the like are properties that impact the imaging in a measurable way. Since, thermoacoustic imaging uses a RF pulsed signal (in one embodiment, at 434 MHz) to generate thermoacoustic (ultrasound) signals in tissue, a thermoacoustic phantom could use a combination of properties or parameters from both MRI and ultrasound imaging.

For a tissue-mimicking material that is used in a multi-modality imaging phantom, additional useful parameters are mechanical strength, uniformity, ease of preparation, low-cost materials, and the like.

Hepatic steatosis is the accumulation of fat in liver tissue. One way to simulate fatty liver in a phantom is to use a two-compartment model with a fat component and a fat free component. The fat free component represents an idealized lean liver with no fat. In one embodiment, the fat free component is made of water, gelatin, L-tyrosine and sodium chloride. In the same embodiment, the fat component is peanut oil. Embodiments using this phantom assume that the composition of lean liver tissue (fat free component) is constant among different individuals and that the variation is only in the fat component.

To simulate the diffuse accumulation of lipids in hepatocytes, the composition should be well-mixed and/or emulsified (for example, using emulsifying agents, immersion blender or high shear mixer) to ensure the uniform distribution of the components.

In one embodiment, a method for preparing the tissue-mimicking material for a multi-modality imaging phantom can include emulsifying the peanut oil with water in the mixture. This can be done using an immersion blender or high-shear homogenizer. Alternatively, this can also be done with the addition of emulsifiers.

In one embodiment, a method for preparing the tissue-mimicking material for a multi-modality imaging phantom can include suspending L-tyrosine in the mixture (which can be heated before or after adding the L-tyrosine). Mixing is required to prevent sedimentation of the L-tyrosine as the temperature of the mixture decreases and approaches the gelation temperature of the gelling agent. The sedimentation rate will decrease enough that mixing can be stopped. The resulting semi-solid phantom has a uniform distribution of L-tyrosine.

For the purposes of this disclosure, the T2 relaxation time of agar is similar to human tissues. For the purposes of this disclosure, a T2 (transverse relaxation time) is the time constant which determines the rate at which excited protons reach equilibrium or go out of phase with each other. Alternately, the time taken for spinning protons to lose phase coherence among nuclei spinning perpendicular to the main field.

For the purposes of this disclosure, the speed of sound in agar is similar to soft tissue.

For the purposes of this disclosure, Zerdine® accurately simulates the ultrasound properties of human liver.

In selected embodiments, the tissue-mimicking materials discussed in the present disclosure can use protein powders to tune dielectric properties while maintaining an overall speed of sound similar to that of soft body tissue (1540 m/s). In some embodiments, a protein powder has a low real-permittivity, does not have lipids (i.e. does not affect fat content of the fat quantification mimicking material). This enables the protein powder to fine-tune the real permittivity for a given phantom or fat quantification mimicking material. The real permittivity is also determined by the amounts of water and oil in the phantom. In conclusion, protein powder enables lowering overall permittivity without increasing the amount of oil.

In selected embodiments, properties of the tissue-mimicking material are tuned to simultaneously match the properties of fatty liver tissue when imaged by thermoacoustic imaging, ultrasound imaging, or MRI fat imaging (GE IDEAL, Philips mDIXON) system. The tissue-mimicking material can also be used for MRI fat quantification (GE IDEAL IQ, Philips mDIXON Quant).

The use of protein powders in tissue mimicking phantoms can be used to make phantoms mimicking other tissue types such as muscle tissue, blood, or the like.

This multi-modality fatty liver phantom can be used as part of a multi-tissue phantom where the other tissues being mimicked can include muscle, subcutaneous fat, visceral fat, blood, skin, or the like.

In addition to fatty liver tissue, other types of fatty tissue that can be mimicked include pancreatic (non-alcoholic fatty pancreatic disease, pancreatic steatosis), muscle (myosteatosis), kidney, heart, or the like.

FIG. 1 shows a perspective view of a multi-modality imaging phantom embodiment. The phantom 10 includes a container 12 having a bottom 14 and walls 15. Preferably the walls 15 include opposed faces 16, and opposed ends 18. Taken together, the bottom, faces, and ends 14, 16, and 18 form a hollow, box-like container structure. Margins of the walls 15 remote from the bottom 14 define a window 20. The window 20 is closed with an ultrasound-transmitting window cover 22. The window cover 22 may be made of any cohesive ultrasound transmitting material of suitable physical durability, such as a thin sheet polyurethane or saran.

The phantom further includes a body 24 of the tissue mimicking material of the present invention. This material substantially fills the container 12 up to the level of the window 20, except as discussed below. The phantom body 24 includes several distinct sections, shown for illustration as four sections 101, 102, 103, and 104 of the tissue mimicking material. One or more of these sections is tissue mimicking material of the present disclosure. As discussed further below, the four sections 101, 102, 103, and 104 may comprise materials which mimic at least the ultrasound, MR, and thermoacoustic properties of four different body tissues. For example, section 101 may have properties that mimic skin, section 102 may have properties that mimic subcutaneous fat, section 103 may have properties that mimic muscle, and section 104 may have properties that mimic liver tissue. The tissue mimicking material of section 104 can be modified to mimic liver tissue with different MRI-PDFF values or percent fat content (by volume or by mass).

Also shown in FIG. 1 are an optional filling hole 32, and optional oil-based gel layer 28, and optional plastic sheet 30.

The container 12 may be filled with the sections 101, 102, 103, and 104 sections of tissue-mimicking material as desired, for example, in the manner described in U.S. Pat. No. 5,625,137, which is herein incorporated by reference in its entirety. Although elements 101, 102, 103, and 104 have been shown for simplicity in FIG. 1 as rectangular sections in contact with each other, as discussed further below, they may be and generally will be formed of other shapes, including shapes simulating human body structures such as a rounded inclusion of section 104 surrounded material of sections 101, 102, and 103.

Figure 2:
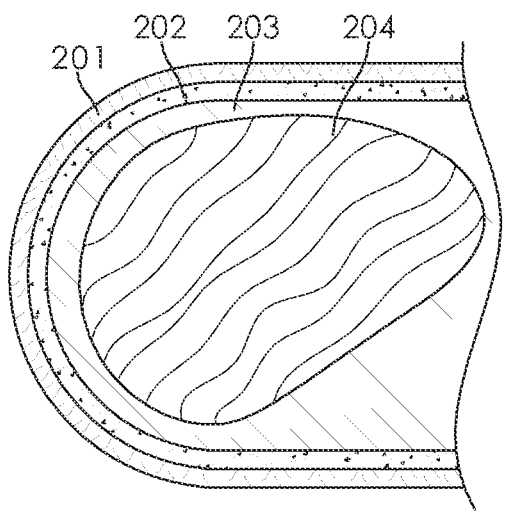
FIG. 2 shows a cross-section of a multi-modality imaging phantom embodiment.

FIG. 2 shows a cross-section of a multi-modality imaging phantom embodiment. Shown are skin section 201, subcutaneous fat section 202, muscle section 203, and liver section 204. In a separate embodiment, the liver section can be replaced with tissue from a different human organ.

The local pressure at a position r may be expressed as the heating function H(r) scaled by a material specific property $\Gamma$, the Grüneisen parameter.

$$p_o(r) = \Gamma H(r) \quad \text{[eq. 1]}$$

The Grüneisen parameter may be expressed as the incremental pressure increase per unit energy increase and is a function of the material's thermal coefficient ($\alpha$) of heat expansion, the speed of sound in the material (u), and the specific heat capacity ($C_p$).

$$\Gamma = V(dV/dE)v = \alpha u^2/C_p \quad \text{[eq. 2]}$$

THE HEATING FUNCTION: Heating by RF and microwave energy is a result of two distinct forms of 'frictional loss' induced by an electric field. Dielectric loss is a frictional damping loss that arises from the reorientation of permanent dipoles of water molecules in the presence of an applied alternating electric field, and is frequency dependent. At RF and microwave frequencies, the water content of tissue dominates the dielectric polarization loss term. The other 'frictional loss' process known as Joule thermal heating, results from electrical current flowing through a conductor in the presence of an applied electric field. The ionic content of tissue determines ionic loss and is generally frequency independent.

Permittivity ($\varepsilon$), is the property that describes a material's ability to store charge in the presence of an electric field. Permittivity ($\varepsilon$) has both a real part and an imaginary part (multiplied by the square root of negative one (i)). The imaginary (i) part of complex permittivity is the sum of the dielectric ($\varepsilon d$) and conductive loss ($\varepsilon c$) terms.

$$\varepsilon = \varepsilon_r + \varepsilon_i i = \varepsilon_r + (\varepsilon_d + \varepsilon_c) i \quad \text{[eq. 3]}$$

The rate of heating Pd (or, energy deposited per unit time) is a function of the energy absorbing, term ($\varepsilon d + \varepsilon c$), and the magnitude of the electric field (E), and is defined by, $$P_d = (\varepsilon_d + \varepsilon_c) |E|^2 \quad \text{[eq. 4]}$$

Consequently, the concentration of water and ion content (conductivity) in tissue strongly defines the thermoacoustic pressure signal induced by RF or microwaves, and gives rise to the tissue contrast mechanism exploited by thermoacoustic techniques. Lean tissue has high water content and high conductivity. Alternatively, fatty tissues contain lipids that are non-polar molecules with very low polarizability and low dielectric loss. Additionally, the ion content (conductivity) of fatty tissue is lower than that of lean tissue. Table 1 below illustrates the complex permittivity (real part ($\varepsilon r$) and imaginary part ($\varepsilon i = \varepsilon d + \varepsilon c$)) for various tissues.

TABLE 1

Complex Permittivity For Different Tissues

| Tissue Type | $\varepsilon_r$ (real part) | $\varepsilon_i$ (imaginary part) |
|---|---|---|
| Blood | 63.8 | 56.3 |
| Muscle | 56.9 | 33.3 |
| Fat | 5.6 | 1.7 |
| Liver (no steatosis) | 52.5 | 27.9 |
| Liver (mild steatosis) | 50.6 | 27.5 |
| Liver (moderate steatosis) | 48 | 26.5 |
| Liver (severe steatosis) | 38.7 | 21.5 |

In practical thermoacoustic imaging and measurement applications, the heating occurs over a very short time on the order of one microsecond. That heating induces a rise in tissue temperature less than 0.01 degrees Celsius. Nonetheless, that tiny, but abrupt, heating is sufficient to generate ultrasound waves deep within tissue that may be detected by conventional ultrasound transducers at the skin surface.

Figure 3:
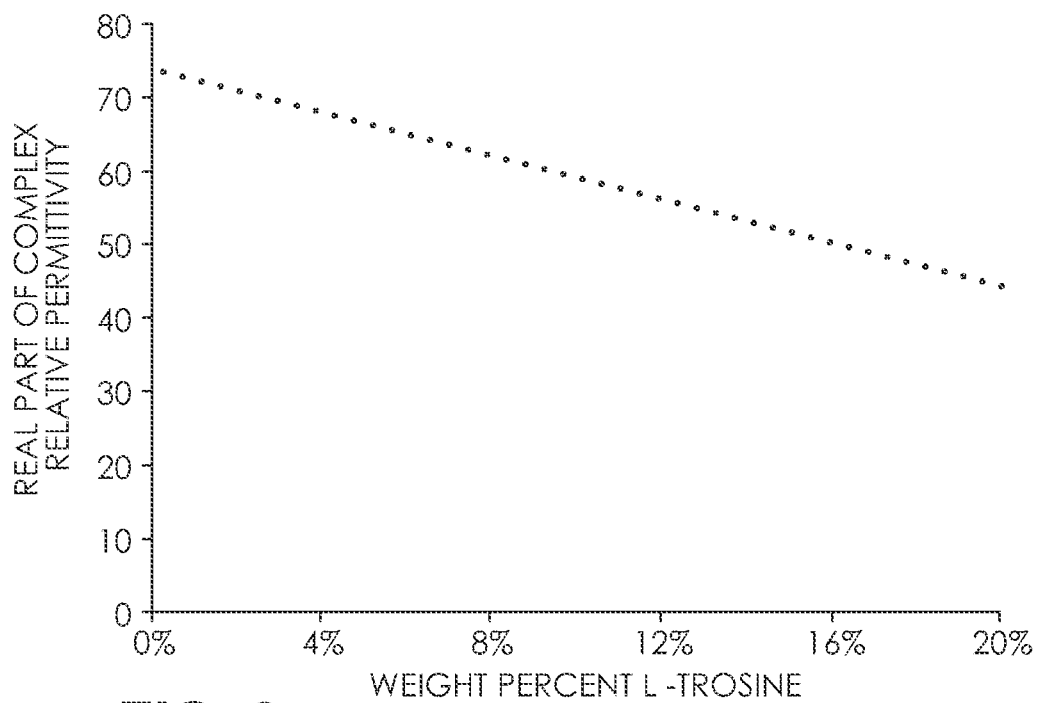
FIG. 3 shows an estimated real part of complex relative permittivity as a function of weight percent L-tyrosine.

FIG. 3 shows an estimated real part of complex relative permittivity as a function of weight percent L-tyrosine at 434 MHz.

Figure 4:
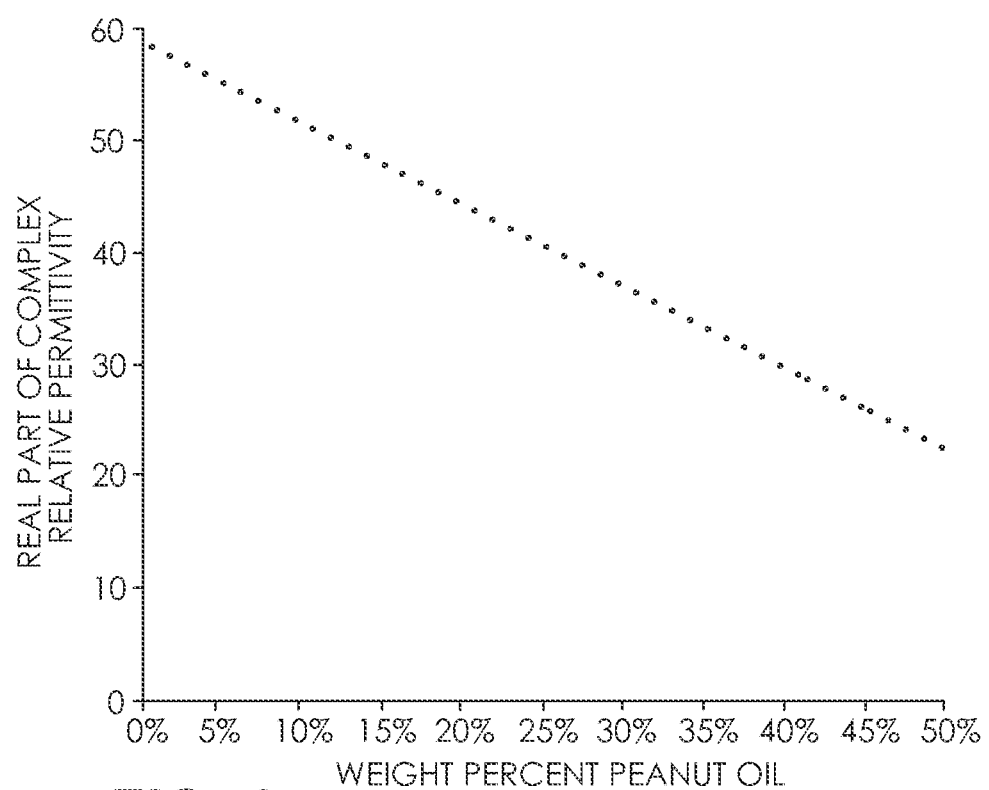
FIG. 4 shows an estimated real part of complex relative permittivity as a function of weight percent peanut oil.

FIG. 4 shows an estimated real part of complex relative permittivity as a function of weight percent peanut oil at 434 MHz.

Figure 5:
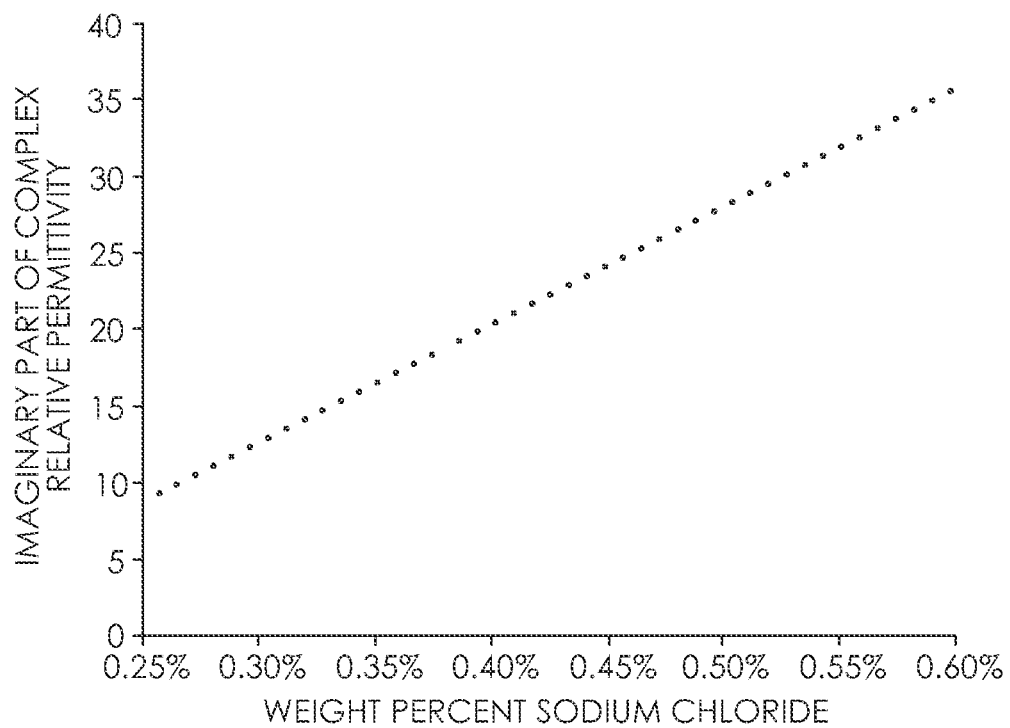
FIG. 5 shows an estimated imaginary part of complex relative permittivity as a function of weight percent sodium chloride.

FIG. 5 shows an estimated imaginary part of complex relative permittivity as a function of weight percent sodium chloride at 434 MHz.

Figure 6:
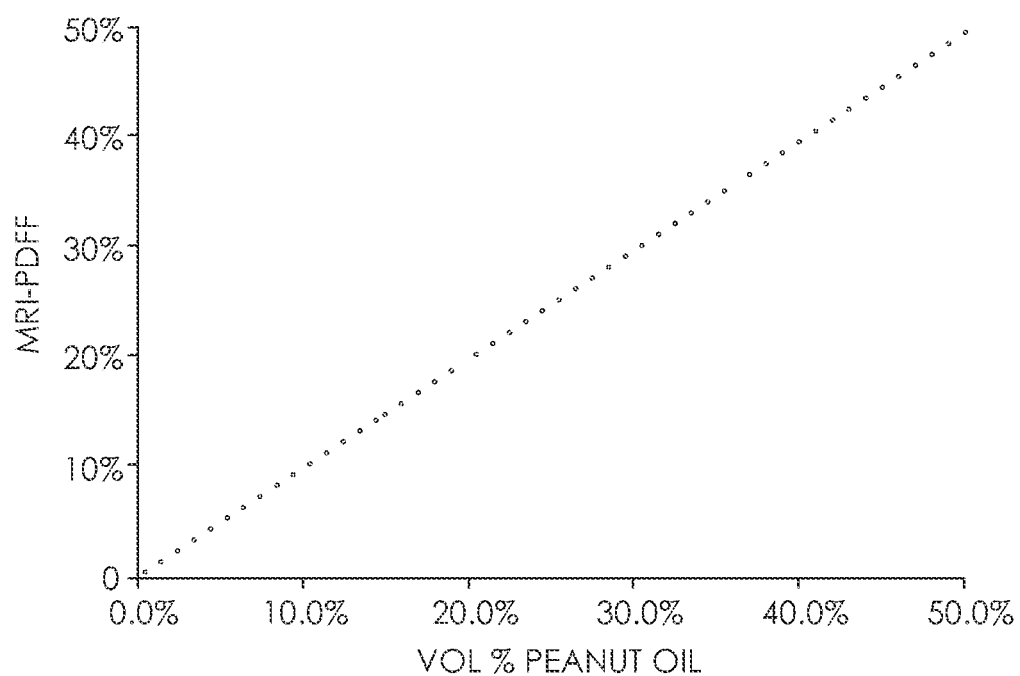
FIG. 6 shows an estimated magnetic resonance imaging (MRI) proton density fat fraction (PDFF) as a function of volume percent peanut oil.

FIG. 6 shows an estimated magnetic resonance imaging (MRI) proton density fat fraction (PDFF) as a function of volume percent peanut oil.

Although embodiments have been described above with reference to the accompanying drawings, those of skill in the art will appreciate that variations and modifications may be made without departing from the scope thereof as defined by the appended claims.

What is claimed is:

1. Multi-modality fatty tissue mimicking material for phantoms for use with thermoacoustic imaging, ultrasound and MRI comprising:
   an aqueous mixture of a 3% to 18% thickening agent, a 1% to 30% protein powder, a 0.1% to 2% ionic salt, a 30% to 85% water, and a 0% to 60% oil by weight, wherein the oil percentage corresponds to the fat percentage in tissue, further wherein the ionic salt percentage corresponds to an imaginary part of complex permittivity in tissue, and further wherein the water, oil and protein powder percentages correspond to the real part of complex permittivity in tissue.

2. The fatty tissue mimicking material of claim 1, wherein the thickening agent is selected from a group consisting of Agar, Agarose, Gelatin, Polyvinyl Alcohol, Sodium Polyacrylate, Sodium Alginate, Acrylamide Hydrogel, Polyacrylamide, Hydroxyethyl Cellulose, Gellan Gum, Guar Gum, Xanthan Gum, Gum Arabic, Gum Tragacanth, Pectin, Carrageenan, Arrowroot, Starches, and some combination thereof.

3. The fatty tissue mimicking material of claim 1, wherein the protein powder is selected from a group consisting of Tyrosine, Proline, Casein, Glycine, Arginine, Methionine, Cystine, Cysteine, Glutamine, Valine, Carnosine, Theanine, Citrulline, Serine, Histidine, Carnitine, Norvaline, Malate, Leucine, Threonine, Ornithine, Albumin, Collagen, Whey, Soy, Pea, Rice, Hemp, and some combination thereof.

4. The fatty tissue mimicking material of claim 1, wherein the ionic salt is selected from a group consisting of Sodium Chloride, Sodium Phosphate, Sodium Fluoride, Sodium Bicarbonate, Sodium Carbonate, Sodium Sulfite, Sodium Hydroxide, Trisodium Citrate, Potassium Iodide, Potassium Phosphate, Potassium Chloride, Magnesium Sulfate, Magnesium Hydroxide, Calcium Carbonate, Aluminum Hydroxide, Silver Iodide, and some combination thereof.

5. The fatty tissue mimicking material of claim 1, wherein the oil is selected from a group consisting of vegetable oil, animal fat, a synthetic alternative, and some combination thereof.

6. The fatty tissue mimicking material of claim 5, wherein the vegetable oil is selected from a group consisting of Peanut Oil, Olive Oil, Soybean Oil, Sesame Oil, Canola Oil, Safflower Oil, Sunflower Oil, Linseed Oil, Rapeseed Oil, Cottonseed Oil, Jojoba Oil, Coconut Oil, *Theobroma* Oil, Avocado Oil, Castor Oil, Corn Oil, Palm Oil, and some combination thereof.

* * * * *